| United States Patent [19] | [11] Patent Number: 4,885,242 |
| Cregg | [45] Date of Patent: * Dec. 5, 1989 |

[54] GENES FROM PICHIA HISTIDINE PATHWAY AND USES THEREOF

[75] Inventor: James M. Cregg, San Diego, Calif.

[73] Assignee: Phillips Petroleum Company, Bartlesville, Okla.

[*] Notice: The portion of the term of this patent subsequent to Jun. 6, 2006 has been disclaimed.

[21] Appl. No.: 666,578

[22] Filed: Oct. 30, 1984

[51] Int. Cl.$^4$ .................. C12P 21/00; C12P 21/02; C12N 15/00; C12N 5/00

[52] U.S. Cl. ........................................ 435/68; 435/91; 435/172.3; 435/70; 435/320; 435/255; 435/256; 435/107; 536/27; 935/6; 935/14; 935/28; 935/37; 935/56; 935/69

[58] Field of Search ............... 435/68, 172.3, 255, 435/317, 256, 253, 107; 536/27; 935/6, 14, 28, 37, 56, 69

[56] References Cited

U.S. PATENT DOCUMENTS 4,617,274 10/1984 Wegner .................. 435/255

OTHER PUBLICATIONS

Orr-Weaver et al, *Chem. Abst.*, vol. 95, No. 200413k, 1981, "Yeast Transformation: A Model System for the Study of Recombination".

Larionov et al, *Chem Abst*, vol. 97, No. 193960x, 1982, "Construction of Hybrid Plasmids Containing Yeast Replicators".

Cryer et al, 1975, *Meth Cell Biol.*, vol. 12, pp. 39-44, "Isolation of Yeast DNA".

Stinchomb et al, *Proc Natl Acad Sci*, 1980, vol. 77, pp. 4554-4563, "Eukanyoric DNA Segments Capable of Autonomous Replication in Yeast".

Hinnen, et al, *Proc Natl Acad Sci*, 1978, vol. 75, pp. 1929-1933, "Transformation of Yeast".

Russell et al, *J Biol Chem*, Jan. 1983, vol. 258, pp. 143-149, "The Primary Structure of the Alcohol Achyaroyenase Gene from the Fission Yeast *Schizosaccharomyces Pombe*".

Donahue et al, *Gene*, vol. 18, pp. 47-59, "The Nucleotide Sequence of the *HIS*4 Region of Yeast".

Mehack et al. *BMBO*, vol. 10 (6), pp. 675-680, Jun. 1982, "Two Yeast Acid Phosphastase Structure Genes are the Result of a Tandem Duplication and Show Different Degrees of Homology in their Promotur and Coding Sequences".

Tuite et al, *BMBO*, vol. 11(5), 1982, pp. 603-608, "Regulated High Efficiency Expression of Human Interferon Alphain Saccharomyces Cerevisiae".

*Primary Examiner*—Robin Teskin
*Attorney, Agent, or Firm*—J. E. Phillips

[57] ABSTRACT

Novel DNA sequences which code for the production of Pichia histidinol dehydrogenase, phosphoribosyl-ATP-cyclohydrase and phosphoribosyl-ATP-pyrophosphohydratase are provided. Novel constructs including these sequences, as well as transformed organisms therewith are provided. A method for isolation of functional genes from yeast strains of the genus Pichia is also provided. In addition, process for the integrative transformation of yeast strains of the genus Pichia is provided.

24 Claims, 6 Drawing Sheets

GENES FROM PICHIA HISTIDINE PATHWAY AND USES THEREOF

BACKGROUND

This invention relates to the field of recombinant DNA technology. In one of its aspects, the invention relates to the isolation of functional genes from yeast strains of the genus Pichia. In another aspect, the invention relates to DNA fragments which regulate expression of a gene product, i.e., a polypeptide. In yet another aspect, the invention relates to the integrative transformation of yeast strains of the genus Pichia.

Up to now, commercial efforts employing recombinant DNA technology for producing various polypeptides have centered on *Escherichia coli* as a host organism. However, in some situations *E. coli* may prove to be unsuitable as a host. For example, *E. coli* contains a number of toxic pyrogenic factors that must be eliminated from any polypeptide useful as a pharmaceutical product. The efficiency with which this purification can be achieved will, of course, vary with the particular polypeptide. In addition, the proteolytic activities of *E. coli* can seriously limit yields of some useful products. These and other considerations have led to increased interest in alternative hosts, in particular, the use of eukaryotic organisms for the production of polypeptide products is appealing.

The availability of means for the production of polypeptide products in eukaryotic systems, e.g., yeast, could provide significant advantages relative to the use of prokaryotic systems such as *E. coli* for the production of polypeptides encoded by recombinant DNA. Yeast has been employed in large scale fermentations for centuries, as compared to the relatively recent advent of large scale *E. coli* fermentations. Yeast can generally be grown to higher cell densities than bacteria and are readily adaptable to continuous fermentation processing. In fact, growth of yeast such as *Pichia pastoris* to ultra-high cell densities, i.e., cell densities in excess of 100 g/L, is disclosed by Wegner in U.S. Pat. No. 4,414,329 (assigned to Phillips Petroleum Co.). Additional advantages of yeast hosts include the fact that many critical functions of the organism, e.g., oxidative phosphorylation, are located within organelles, and hence not exposed to the possible deleterious effects of the organism's production of polypeptides foreign to the wild-type host cells. As a eukaryotic organism, yeast may prove capable of glycosylating expressed polypeptide products where such glycosylation is important to the bioactivity of the polypeptide product. It is also possible that as a eukaryotic organism, yeast will exhibit the same codon preferences as higher organisms, thus tending toward more efficient production of expression products from mammalian genes or from complementary DNA (cDNA) obtained by reverse transcription from, for example, mammalian mRNA.

The development of poorly characterized yeast species as host/vector systems is severely hampered by the lack of knowledge about transformation conditions and suitable vectors. In addition, auxotrophic mutations are often not available, precluding a direct selection for transformants by auxotrophic complementation. If recombinant DNA technology is to fully sustain its promise, new host/vector systems must be devised which facilitate the manipulation of DNA as well as optimize expression of inserted DNA sequences so that the desired polypeptide products can be prepared under controlled conditions and in high yield.

A basic element employed in recombinant DNA technology is the plasmid, which is extrachromosomal, double-stranded DNA found in some microorganisms. Where plasmids have been found to naturally occur in microorganisms, they are often found to occur in multiple copies per cell. In addition to naturally occurring plasmids, a variety of man-made plasmids, or hybrid vectors, have been prepared. Included in the information encoded in plasmid DNA is that required to reproduce the plasmid in daughter cells, i.e., an autonomous replication sequence. One or more phenotypic selection characteristics must also be included in the information encoded in the plasmid DNA. The phenotypic selection characteristics permit clones of the host cell containing the plasmid of interest to be recognized and selected by preferential growth of the cells in selective media.

OBJECTS OF THE INVENTION

An object of the invention is therefore funtional genes from yeast strains of the genus Pichia, useful, for example, as phenotypic selection markers.

Another object of the invention is novel regulatory regions which are responsive to the presence or absence of amino acids in the culture medium.

Yet another object of the invention is the integrative transformation of yeast strains of the genus Pichia.

A further object of the invention is a process for producing polypeptides employing the novel DNA fragments of the invention as phenotypic selection markers and/or as regulatory regions.

These and other objects of the invention will become apparent from the disclosure and claims herein provided.

STATEMENT OF THE INVENTION

In accordance with the present invention, I have discovered, isolated and characterized the HIS4 gene from a strain of yeast of the genus Pichia. In addition, I have developed a general procedure for the isolation of functional genes from yeast strains of the genus Pichia. The novel genes which I have isolated are useful as phenotypic selection markers in a host/vector system employing yeast strains of the genus Pichia as host.

In accordance with another embodiment of the invention, I have discovered, isolated and characterized a regulatory region responsive to the presence or absence of amino acids in the culture medium. This regulatory region is useful, for example, for the controlled expression of polypeptide products in yeast.

In accordance with yet another embodiment of the invention, a process for the integrative transformation of yeast of the genus Pichia has been developed. This method of transforming yeast provides a means for recombination of vector sequences into the chromosomal DNA of the host. This recombination results in stable maintenance of inserted DNA sequences in the host chromosomal DNA. Stable maintenance of inserted sequences is accomplished without the requirement for selective growth conditions for cell maintenance of inserted DNA sequences as extrachromosomal DNA.

The following abbreviations are used throughout this specification to represent the restriction enzymes employed:

| Abbreviation | Restriction Enzyme |
|---|---|
| B | Bam HI |
| $B_2$ | Bgl II |
| C | Cla I |
| $H_3$ | Hind III |
| Nr | Nru I |
| Ps | Pst I |
| $Pv_2$ | Pvu II |
| $R_1$ | Eco RI |
| $R_5$ | Eco RV |
| S | Sal I |
| Sm | Sma I |
| Sp | Sph I |
| Ss | Sst I |
| $S_3$ | Sau 3A |
| T | Taq I |
| Xb | Xba I |
| Xh | Xho I |

In the attached figures, restriction sites employed for the manipulation of DNA fragments but which are destroyed upon ligation, are indicated by enclosing the abbreviation for the destroyed site in parenthesis. Restriction sites which have been destroyed by other means are indicated by flagging the abbreviation for the destroyed site with an asterisk.

DETAILED DESCRIPTION OF THE INVENTION

In accordance with one embodiment of the present invention, there is provided a method for isolation of functional genes from yeast strains of the genus Pichia. The method is based on the recognition that Pichia genes and gene products have the ability to complement the defects in Saccharomyces cerevisiae mutant host strains, and thereby reverse the host mutant phenotypes. The method comprises:

(1) Transformation of defective Saccharomyces cerevisiae strains with fragments of Pichia chromosomal DNA, which have been recombined into S. cerevisiae-E. coli shuttle vectors;

(2) Selection of transformed strains by their ability to survive and grow in selective growth media, wherein the selective growth media are specifically devoid of the nutrients or do not provide the conditions required by the defective host strain for growth;

(3) Isolation and recovery of Pichia DNA fragments which contain the desired genes from the plasmids contained in the selected transformed strains.

It has been discovered that the functional genes from microorganisms of the genera Pichia and Saccharomyces are sufficiently similar to allow one to take advantage of well-characterized defective strains of Saccharomyces cerevisiae in order to isolate complementary functional genes from Pichia. For example, I have isolated genes equivalent to the Saccharomyces HIS3 and HIS4 genes from Pichia. These novel genes which I have isolated are referred to for purposes of this disclosure as the Pichia HIS3 and HIS4 genes. These novel genes have been isolated by transforming appropriate mutants of S. cerevisiae with a library of Pichia chromosomal DNA and selecting for transformed strains which survive in the absence of histidine supplementation in the media. Those of skill in the art recognize that one could isolate the Pichia LEU2 gene by transforming a leu2 S. cerevisiae mutant with a library of Pichia chromosomal DNA and selecting for transformed strains which survive in the absence of leucine supplementation of the media. Similarly, one could isolate the Pichia ARG4 gene by transforming an appropriate S. cerevisiae mutant with a library of Pichia chromosomal DNA and proceeding as above, except the selection media would be absent arginine supplementation.

Isolation and Characterization of *Pichia pastoris* HIS4 Gene

Figure 1:
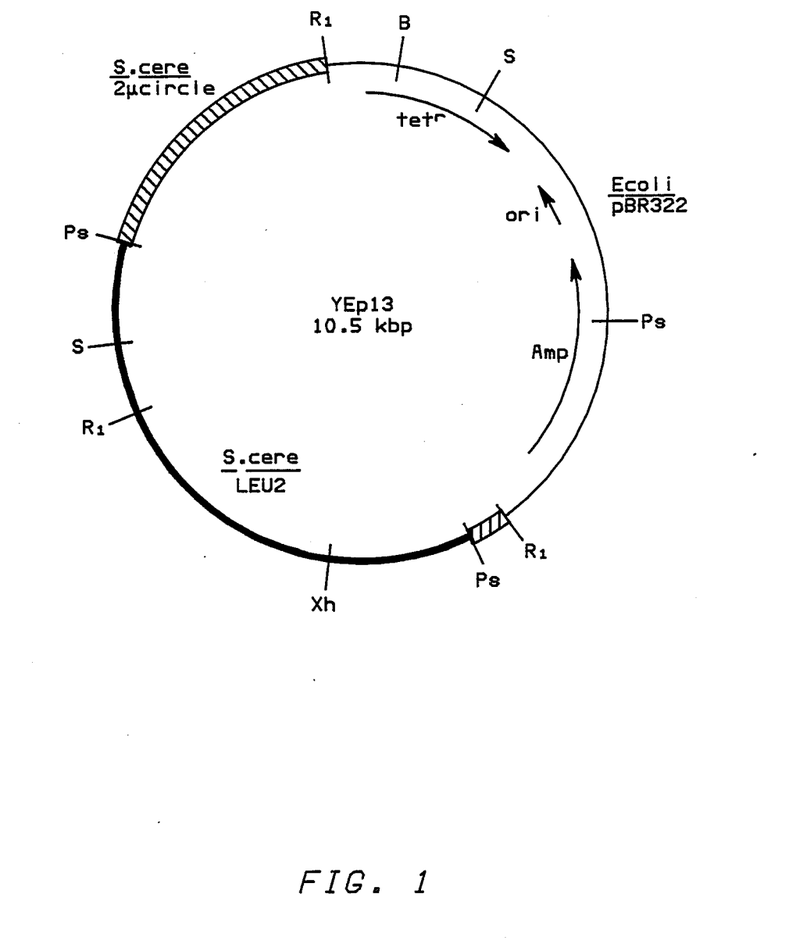
FIG. 1 is a restriction map of plasmid YEp13.
Figure 2:
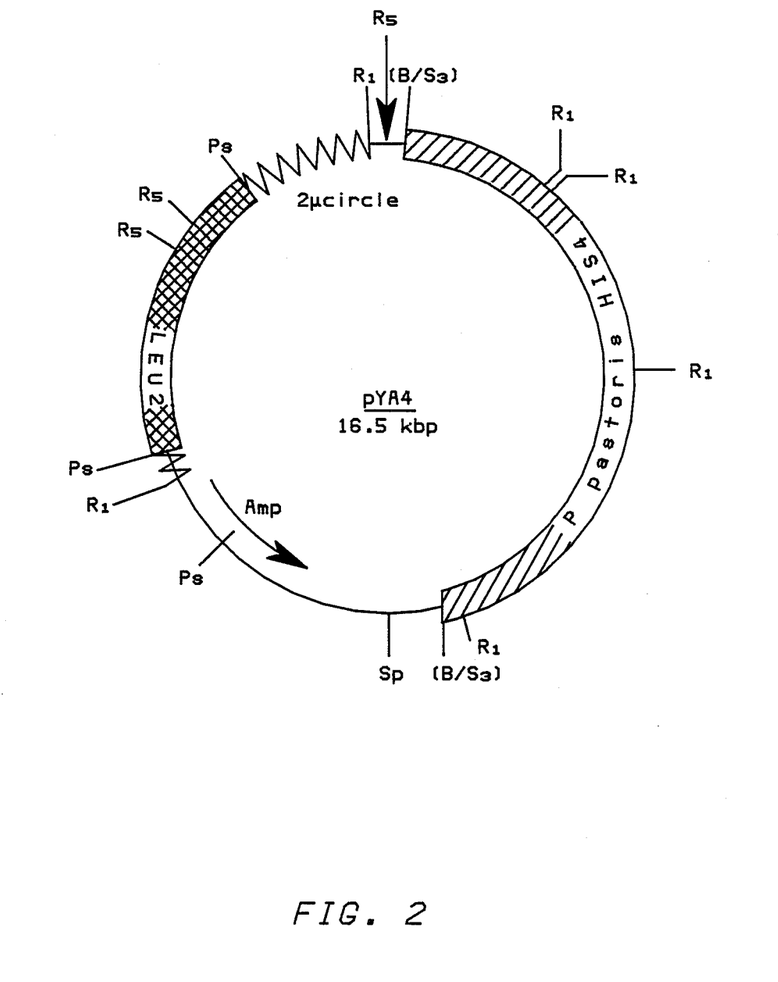
FIG. 2 is a restriction map of plasmid pYA4.
Figure 4:
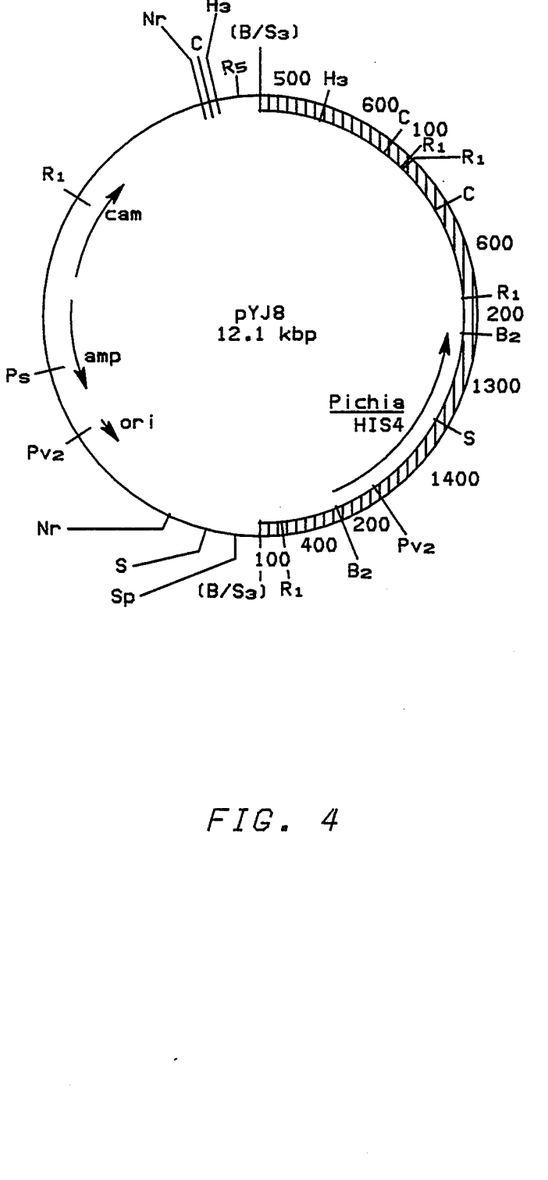
FIG. 4 is a restriction map of plasmid pYJ8.

The HIS4 gene was isolated from the strain P. pastoris NRRL Y-11430 by partial digestion of total chromosomal DNA with Sau3A followed by centrifugation through sucrose graidents. (See Example II). Fragments of 5 to 20 kbp were cloned into the BamHI cleavage site of the S. cerevisiae-E. coli shuttle vector YEp13 (ATCC 37115; FIG. 1) and transformed into E. coli. Approximtely 50,000 colonies were combined and total plasmid DNA extracted. Spheroplastis of S. cerevisiae strain 5799-4D (NRRL Y-15859), a his4ABC mutant, were mixed with about 1 $\mu$g of the YEp13 Pichia DNA library by the procedure of Hinnen et al (1978) and allowed to regenerate in a medium deficient in histidine. The transformation resulted in about $1 \times 10^3$ prototrophic yeast colonies from a population of $5 \times 10^7$ total regenerable spheroplasts. A parallel control sample incubated without DNA produced no colonies. Total yeast DNA was extracted from 20 of the His+ colonies and transformed back into E. coli. Seventeen of the yeast DNA preparations produced ampicillin resistant colonies. These cloned fragments were further characterized by restriction enzyme sizing and mapping as well as by their ability to cross hybridize with a labelled S. cerevisiae HIS4 fragment at low stringency (post hybridization washes in 2×SSC at 55°; SSC is 0.15M NaCl and 15 mM sodium citrate adjusted to pH 7.0 with NaOH). Most of the plasmids contained one or more fragments which hybridized to the S. cerevisiae HIS4 gene. One such HIS4-containing plasmid was recloned to give a HIS4-containing plasmid designated pYJ8 and is shown in FIG. 4. Plasmid pYJ8 contains pBR325 sequences, including functional chloramphenicol and ampicillin resistance genes, as well as the Pichia HIS4 gene.

Figure 3:
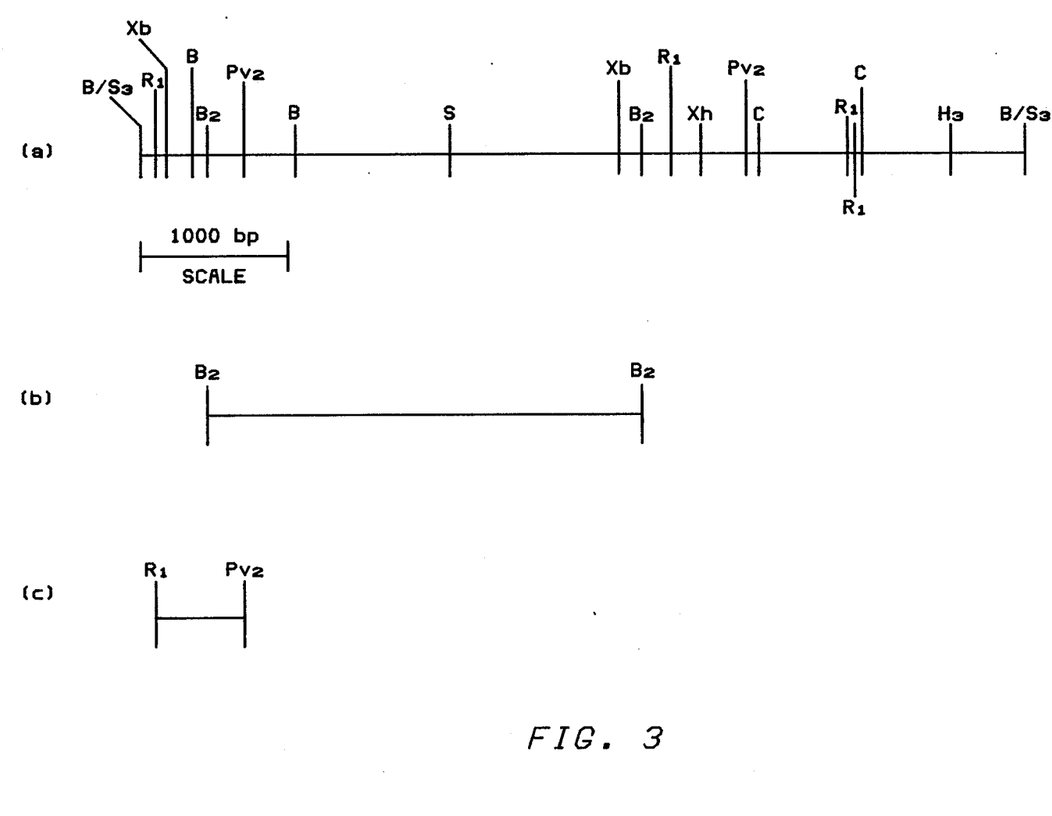
FIG. 3 is a restriction map of a 6.0 kilobase pair (kbp) fragment of Pichia chromosomal DNA which contains the Pichia HIS4 gene. Also shown are specific subfragments of interest.

A detailed restriction map of the Pichia HIS4 gene, which comprises the enzyme activities for histidinol dehydrogenase, phosphoribosyl-ATP-cyclohydrase and phosphoribosyl-ATP-pyrophosphohydratase, is presented in FIG. 3a. Referring to the 5' end of the 6 kbp DNA fragment as the origin, the following cleavage pattern is obtained:

| Restriction Enzyme | Cleavage sites | Distance from origin (bp) |
|---|---|---|
| $R_1$ | 4 | 200, 3900, 4900, 5050 |
| Xb | 2 | 450, 3400 |
| B | 2 | 700, 1100 |
| $B_2$ | 2 | 750, 3500 |
| $Pv_2$ | 2 | 850, 4300 |

| Restriction Enzyme | Cleavage sites | Distance from origin (bp) |
| --- | --- | --- |
| S | 1 | 2300 |
| Xh | 1 | 4100 |
| C | 2 | 4550, 5100 |
| H₃ | 1 | 5550 |

Figure 5:
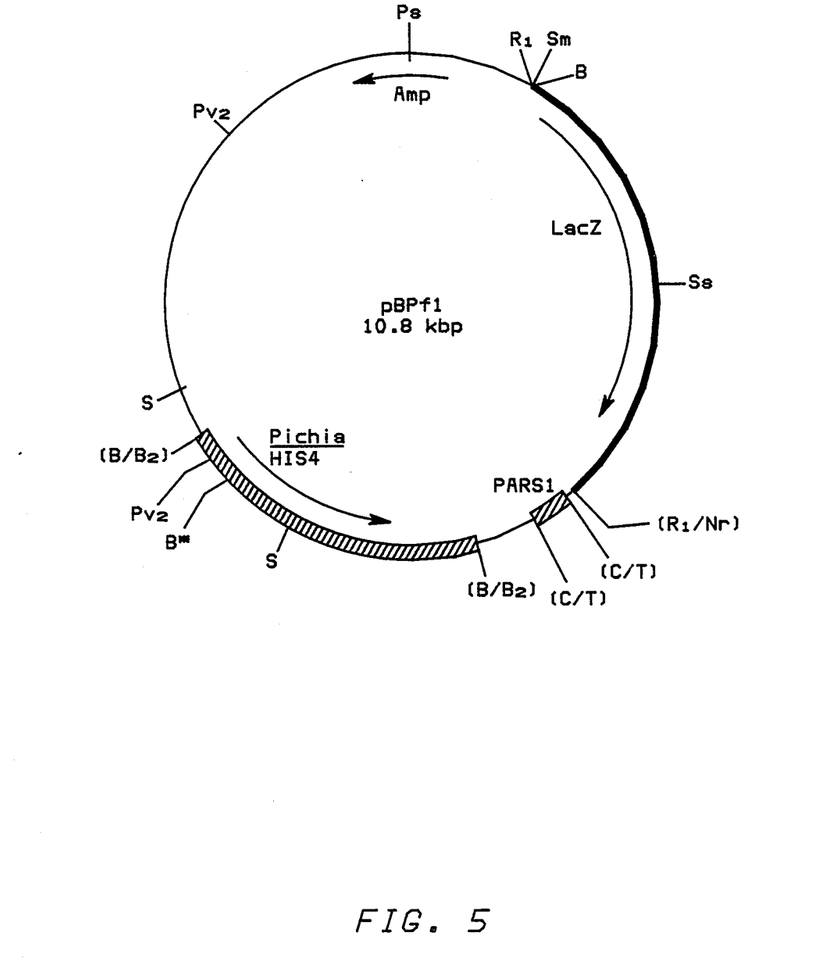
FIG. 5 is a restriction map of plasmid pBPf1.

By subcloning of this 6.0 kbp fragment, it was determined that a 2.7 kbp BglII fragment of this Pichia DNA retained the ability to transform Pichia or Saccharomyces strains defective in HIS4A, HIS4B, or HIS4C gene encoded activities. Thus, for example, Pichia pastoris NRRL Y-15851 (GS115), a his4 mutant, is able to grow on media without histidine supplementation when transformed with plasmid pBPf1, shown in FIG. 5. Plasmid pBPf1 contains the 2.7 kbp BglIII fragment of Pichia chromosomal DNA, shown in FIG. 3b of the drawings.

In order to increase the utility of pBPf1, the BamHI site within the 2.7 kbp BglII fragment which contains the Pichia HIS4 gene was destroyed prior to incorporating this fragment into pBPf1. Thus, the Pichia HIS4 gene, contained in a vector with no other BamHI sites, was cleaved with BamHI and the resulting sticky ends were filled in with a mixture of all 4 deoxynucleotides in the presence of DNA polymerase I to produce blunt ends. The newly-created blunt ends were ligated to give a modified HIS4 gene without a BamHI recognition site. This modified HIS4 gene was the source of the 2.7 kbp BglII fragment used in the construction of plasmid pBPf1. The location of the destroyed BamHI site is designated by B* in FIGS. 5 and 6. Note that the BamHI site in the polylinker of pBPf1 is a unique restriction site for the vector. In addition, the further presence of unique EcoRI and SmaI restriction sites makes pBPf1 a vector useful for exploring the ability of DNA fragments to promote and/or regulate the expression of a gene product in transformed Pichia pastoris.

In accordance with another embodiment of the invention, a DNA fragment comprising a regulatory region responsive to the presence or absence of amino acids in the culture medium has been isolated and characterized. Thus in FIG. 3c, an approximately 600 bp EcoRI-PvuII fragment of DNA obtained from the 5′ end of the 6.0 kbp fragment containing the Pichia HIS4 gene is shown. This fragment is responsive to the presence or absence of amino acids in the culture medium. In a rich medium such as YPD, the regulatory region is "off", i.e., Pichia HIS4 gene encoded products are no longer synthesized. Conversely, when histidine is present in low concentration in the culture medium, the regulatory region "turns on", i.e., Pichia HIS4 gene encoded products are synthesized.

Figure 6:
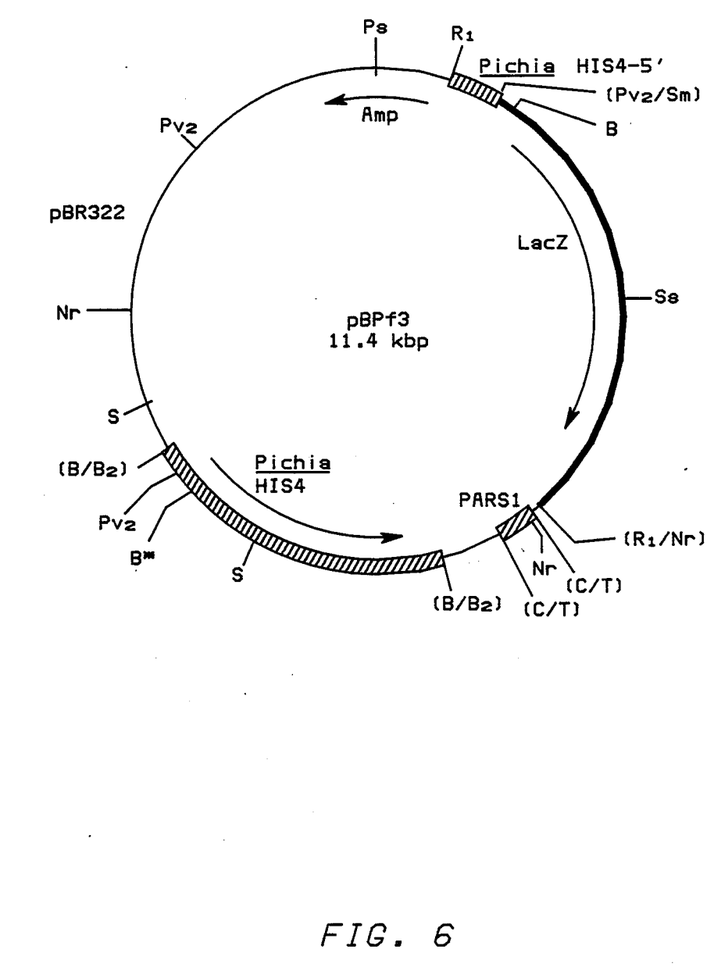
FIG. 6 is a restriction map of plasmid pBPf3.

The control of polypeptide production under the control of this novel regulatory region has been demonstrated with the novel plasmid, pBPf3, shown in FIG. 6. The plasmid contains, inter alia, the HIS4 regulatory region and the LacZ gene. Pichia pastoris NRRL Y-15851 transformed with plasmid pBPf3 produces significant quantities of β-galactosidase when grown in media devoid of histidine but produces at least 10-fold less β-galactosidase when grown in a rich medium such as YPD, which includes histidine.

Integrative Transformation of Pichia

In accordance with yet another embodiment of the invention, a process for integrative recombination of plasmid sequences into the genome of yeast strains of the genus Pichia is provided. The process of integrative recombination is referred to for purposes of this disclosure as "integrative transformation."

The transformation of Pichia pastoris has not been previously described. The experimental procedures for transformation of Pichia pastoris are presented in greater detail below (Example I). In order to develop a transformation system for P. pastoris, the auxotrophic mutant (GS115) NRRL Y-15851 was isolated and determined to be defective in the histidine pathway in that the strain has no detectable histidinol dehydrogenase activity.

Yeast strains of the genus Pichia can be transformed by enzymatic digestion of the cell walls to give spheroplasts; the spheroplasts are then mixed with the transforming DNA and incubated in the presence of calcium ions and polyethylene glycol, then regenerated in selective growth medium. The transforming DNA includes the functional gene in which the host strain is deficient, thus only transformed cells survive and grow on the selective medium employed.

Integrative transformation of Pichia can be accomplished by employing as the transforming DNA a vector comprising:
(i) a gene which can be selected in the Pichia host strain being transformed;
(ii) Pichia DNA sequences which have a substantial degree of homology with the genome of the Pichia host strain; and
(iii) additional DNA fragments selected from the group consisting of:
   regulatory regions, and
   polypeptide coding regions,
   wherein the transforming DNA material contains essentially no autonomous replication sequence activity in Pichia. Optionally, the transforming DNA can further comprise:
(iv) DNA sequences having a bacterial origin of replication and at least one marker selectible in bacteria. The further inclusion of the DNA sequences as described in (iv) facilitates production of DNA in large quantities by allowing for propogation in bacteria. In addition, inclusion of these sequences may provide additional unique restriction sites useful for further modification of the tranforming DNA.

A suitable integrative transformation vector is represented by plasmid pYJ8, shown in FIG. 4. Transformation of a host such as Pichia pastoris NRRL Y-15851 with plasmid pYJ8, or a derivative of pYJ8 containing additional DNA sequences, will lead to integration of the plasmid DNA into the chromosome of the host. This results from the substantial degree of homology between the defective gene of the auxotrophic mutant and the functional gene provided by the plasmid, and the purposeful absence of an ARS element in the plasmid. Unless integration occurs, a plasmid without an ARS element has no means of being passed on to daughter cells and therefore will be "lost" from future generations of host cells. The homology between the Pichia-derived DNA sequences of the transforming vector and the host genomic sequences provides the driving force for recombination of the vector and host DNA. As a result, plasmid DNA becomes integrated into the host chromosome.

EXAMPLES

The buffers and solutions employed in the following examples have the compositions given below:

| | |
|---|---|
| 1M Tris buffer | 121.1 g 34 base in 800 mL of H$_2$O; adjust pH to the desired value by adding concentrated (35%) aqueous HCl; allow to cool to room temperature before final pH adjustment; dilute to a -filter of 1L. |
| TE buffer | 1.0 mM EDTA in 0.01 M (pH 7.4) Tris buffer |
| LB (Luria-Bertani) Medium | 5 -filter 5 g Bacto-yeast extract 2.5 g NaCl in 1 L of water, adjusted to pH 7.5 with NaOH |
| 2B Medium | 0.2% NH$_4$PO$_4$ 1.2% Na$_2$HPO$_4$ 0.013% MgSO$_4$ . 7H$_2$O 0.074% CaCl$_2$ .68c 2H$_2$O 1 µg/mL thiamine 0.4% dextrose |
| YPD Medium | 1% Bacto-yeast extract 2% Bacto-peptone 2% Dextrose |
| SD Medium | 6.75 g yeast nitrogen base without amino acids (DIFCO) 2% Dextrose in 1 L of water |
| HAM | 0.67% yeast nitrogen base without amino acids (DIFCO) 1% dextrose 2% histidine assay medium (DIFCO) 50 µg/mL each of: isoleucine leucine lysine methionine glutamine |
| SED | 1 M Sorbitol 25 mM EDTA 50 mM DTT |
| SCE Buffer | 9.1 g Sorbitol 1.47 g Sodium citrate 0.168 g EDTA 50 mL H$_2$O —pH to 5.8 with HCl |
| CaS | 1 M Sorbitol 10 mM CaCl$_2$ —filter sterilize |
| PEG Solution | 20% polyethylene glycol-3350 10 mM CaCl$_2$ 10 mM Tris-HCl (pH 7.4) —filter sterilize |
| SOS | 1 M Sorbitol 0.3x YPD medium 10 mM CaCl$_2$ |

The following abbreviations are used throughout the examples with the following meaning:

| | |
|---|---|
| EDTA | ethylenediamine tetraacetic acid |
| SDS | sodium dodecyl sulfate |
| DTT | dithiothreitol |

EXAMPLE I

*Pichia pastoris* Transformation Procedure

A. Cell Growth

1. Inoculate a colony of *Pichia pastoris* GS115 (NRRL Y-15851) into about 10 mL of YPD medium and shake culture at 30° C. for 12-20 hrs.

2. After about 12-20 hrs., dilute cells to an OD$_{600}$ of about 0.01-0.1 and maintain cells in log growth phase in YPD medium at 30° C. for about 6-8 hrs.

3. After about 6-8 hrs, inoculate 100 mL of YPD medium with 0.5 mL of the seed culture at an OD$_{600}$ of about 0.1 (or equivalent amount). Shake at 30° C. for about 12-20 hrs.

4. Harvest culture when OD$_{600}$ is about 0.2-0.3 (after approximately 16-20 hrs) by centrifugation at 1500 g for 5 minutes.

B. Preparation of Spheroplasts

1. Wash cells once in 10 mL of sterile water. (All centrifugations for steps 1-5 are at 1500 g for 5 minutes.)

2. Wash cells once in 10 mL of freshly prepared SED.

3. Wash cells twice in 10 mL of sterile 1M Sorbitol.

4. Resuspend cells in 10 mL SCE buffer.

5. Add 5-10 µL of 4 mg/mL Zymolyase 60,000 (Miles Laboratories). Incubate cells at 30° C. for about 30-60 minutes.

Since the preparation of spheroplasts is a critical step in the transformation procedure, one should monitor spheroplast formation as follows: add 100 µL aliquots of cells to 900 µL of 5% SDS and 900 µL of 1M Sorbitol before or just after the addition of zymolyase and at various times during the incubation period. Stop the incubation at the point where cells lyse in SDS but not in sorbitol (usually between 30 and 60 minutes of incubation).

6. Wash spheroplasts twice in 10 mL of sterile 1M Sorbitol by centrifugation at 1000 g for 5-10 minutes. (The time and speed for centrifugation may vary; centrifuge enough to pellet spheroplasts but not so much that they rupture from the force.)

7. Wash cells once in 10 mL of sterile CaS.

8. Resuspend cells in total of 0.6 mL of CaS.

C. Transformation

1. Add DNA samples (up to 20 µL volume) to 12×75 mm sterile polypropylene tubes. (DNA should be in water or TE buffer; for maximum transformation frequencies with small amounts of DNA, it is advisable to add about 1 µL of 5 mg/mL sonicated *E. coli* DNA to each sample.)

2. Add 100 µL of spheroplasts to each DNA sample and incubate at room temperature for about 20 minutes.

3. Add 1 mL of PEG solution to each sample and incubate at room temperature for about 15 minutes.

4. Centrifuge samples at 1000 g for 5-10 minutes and decant PEG solution.

5. Resuspend samples in 150 µL of SOS and incubate for 30 minutes at room temperature.

6. Add 850 µL of sterile 1M Sorbitol and plate aliquots of samples as described below.

D. Regeneration of Spheroplasts

1. Recipe for Regeneration Agar Medium:
   a. Agar-Sorbitol-9 g Bacto-agar, 54.6 g Sorbitol, 240 mL H$_2$O, autoclave.
   b. 10X Glucose-20 g Dextrose, 100 mL H$_2$O, autoclave.
   c. 10X SC-6.75 g Yeast Nitrogen Base without amino acids, 100 mL H$_2$O, autoclave. (Add any desired amino acid or nucleic acid up to a concentration of 200 µg/mL before or after autoclaving.)
   d. Add 30 mL of 10X Glucose and 30 mL of 10X SC to 300 mL of the melted Agar-Sorbitol solution. Add 0.6 mL of 0.2 mg/mL biotin and any other desired amino acid or nucleic acid to a concentration of 20 µg/mL. Hold melted Regeneration Agar at 55°-60° C.

2. Plating of Transformation Samples:
   Pour bottom agar layer of 10 mL Regeneration Agar per plate at least 30 minutes before transformation samples are ready. Distribute 10 mL aliquots of Regeneration Agar to tubes in a 45°–50° C. bath during the period that transformation samples are in SOS. Add aliquots of transformation samples described above to tubes with Regeneration Agar and pour onto bottom agar layer of plates. Add a quantity of each sample to 10 mL aliquots of melted Regeneration Agar held at 45°–50° C. and pour each onto plates containing a solid 10 mL bottom agar layer of Regenation Agar.

3. Determination of Quality of Spheroplast Preparation:

Remove 10 μL of one sample and dilute 100 times by addition to 990 μL of 1M Sorbitol. Remove 10 μL of the 100 fold dilution and dilute an additional 100 times by addition to a second 990 μL aliquot of 1M Sorbitol. Spread plate 100 μL of both dilutions on YPD agar medium to determine the concentration of unspheroplasted whole cells remaining in the preparation. Add 100 μL of each dilution to 10 mL of Regeneration Agar supplemented with 40 μg/mL histidine to determine total regeneratable spheroplasts. Good values for a transformation experiment are $1–3 \times 10^7$ total regeneratable spheroplasts/mL and about $1 \times 10^3$ whole cells/mL.

4. Incubate plates at 30° C. for 3–5 days.

EXAMPLE II

Isolation Of *Pichia Pastoris* HIS4 Gene

A. Strains

The strains employed include:
(a) *Pichia pastoris* strain NRRL Y-11430;
(b) *Pichia pastoris* strain NRRL Y-15851 (GS115-his4);
(c) *S. cerevisiae* strain 5799-4D (a his4-260 his4-39; NRRL Y-15859); and
(d) *E. coli* strain 848 (F− met thi gal $T_1^R$ $\phi 80^S$ hsdR− hsdM+).

B. Plasmids pYA2, which consists of the *S. cerevisiae* HIS4 gene on a 9.3 kbp PstI fragment inserted at the PstI site of pBR325 was the source of the *S. cerevisiae* HIS4 gene fragments and has been deposited in an *E. coli* host and is available to the public as NRRL B-15874.

YEp13 is available from the American Type Culture Collection and has been assigned accession number ATCC 37115.

C. Media

*Pichia pastoris* was grown in YPD (rich) or IMG (minimal) media. IMG, a minimal medium, consists of the following:

1. $IM_1$ Salts at a final concentration of 36.7 mM $KH_2PO_4$, 22.7 mM $(NH_4)_2SO_4$, 2.0 mM $MgSO_4.7H_2O$, 6.7 mM KCl, 0.7 mM $CaCl_2.2H_2O$, prepared as a 10× stock solution and autoclaved;
2. Trace Salts at a final concentration of 0.2 μM $CuSO_4.5H_2O$, 1.25 μM KI, 4.5 μM $MnSO_4.H_2O$, 2.0 μM $NaMoO_4.2H_2O$, 0.75 μM $H_3BO_3$, 17.5 μM $ZnSO_4.7H_2O$, 44.5 μM $FeCl_3.6H_2O$, prepared as a 400× stock solution and filter sterilized;
3. 0.4 μg/mL biotin; and
4. 2% dextrose.

*E. coli* was cultured in either LB medium or 2B medium supplemented with 100 μg/mL tryptophan, and 0.2% Casamino acids.

D. DNA Isolation

1. Large Scale Preparations of Yeast DNA.

Both *Pichia pastoris* and *S. cerevisiae* DNA preparations were carried out by growing yeast cells in 100 mL of minimal medium until $A_{600}$ equals 1–2 and then harvesting the cells by centrifugation at 2,000 g for 5 minutes. The cells were washed once in $H_2O$, once in SED, once in 1M sorbitol and then suspended in 5 mL of 0.1M Tris-HCl (pH 7.0) which is 1M in sorbitol. The cells were mixed with 50–100 μL of a 4 mg/mL solution of Zymolase 60,000 (Miles Laboratories) and incubated at 30° C. for 1 hour to digest the cell walls. The spheroplast preparation was then centrifuged at 1000 g for 5–10 minutes and suspended in Lysis buffer (0.1% SDS, 10 mM Tris-HCl, (pH 7.4), 5 mM EDTA and 50 mM NaCl). Proteinase K (Boehringer Mannheim) and RNase A (Sigma) were each added to 100 μg/mL and the mixture incubated at 37° C. for 30 minutes. DNA was deproteinized by gently mixing the preparation with an equal volume of chloroform containing isoamyl alcohol (24:1, v/v) and the phases were separated by centrifugation at 12,000 g for 20 minutes. The upper (aqueous) phase was drawn off into a fresh tube and extracted with an equal volume of phenol/chloroform-/isoamyl alcohol (25:24:1, v/v/v). The phases were separated as before and the top phase placed in a tube containing 2–3 volumes of cold 100% ethanol. The sample was gently mixed and DNA was collected by spooling onto a plastic rod. The DNA was immediately dissolved in 1 mL of TE buffer and dialyzed overnight at 4° C. against 100 volumes TE buffer.

2. Small Scale Yeast DNA Preparations.

Five mL of yeast cultures in minimal medium were grown until $A_{500}$ equals 1–5 and harvested by centrifugation at 2,000 g for 5 minutes. Cells were suspended in 1 mL of SED and transferred to a 1.5 mL microfuge tube, washed once in 1M sorbitol and resuspended in 0.5 mL of 0.1M Tris-HCl (pH 7.4) which is 1M sorbitol. Zymolyase 60,000 (Miles Laboratories; 10 μL of a 4 mg/mL solution) was added to each sample and the cells were incubated for 30–60 minutes at 30° C. Cells were then centrifuged for 1 minute, suspended in the Lysis buffer and incubated at 65°–70° C. After 15 minutes the samples were mixed with 100 μL of 5M potassium acetate, held in an ice bath for 15 minutes and centrifuged for 5 minutes. The supernatants were decanted into a fresh microfuge tube containing 1 mL of 100% ethanol, mixed and immediately centrifuged for 10 seconds. Finally, the DNA pellets were air dried for 10–15 minutes and dissolved in 50 μL of TE buffer.

3. Large Scale *E. coli* DNA Preparations.

*E. coli* cultures for large scale (0.5–1 L) plasmid preparations were grown at 37° C. with shaking in 2B medium supplemented as described above and with the appropriate antibiotic. For cells which contained pBR322 derived plasmids, cultures were grown to an $A_{550}$ of about 0.7 at which time sufficient chloramphenicol was added to give a concentration of 100 μg/mL and cells harvested approximately 15 hours later. Strains which contained pBR325 derived plasmids were inoculated into the supplemented 2B medium at a starting $A_{550}$ of about 0.01–0.05 and incubated with shaking at 37° C. for 20–24 hours before harvesting. Plasmids were isolated by the alkaline lysis method described by Birnboim and Doly (1979).

4. Small Scale *E. coli* DNA Preparations.

For small scale rapid plasmid isolations, 2 mL cultures in the supplemented 2B medium with antibiotic were grown overnight at 37° C. with shaking and harvested by centrifugation in 1.5 mL microfuge tubes. Plasmids were isolated by the alkaline lysis method described by Birnboim and Doly (1979).

E. Restriction of DNA and Fragment Isolation

Restriction enzymes were obtained from New England Biolabs and Bethesda Research Laboratories and digestions were performed by routine techniques. Restriction mappings were carried out by comparing parallel digestions of plasmids with and without insert DNA. Restriction fragments were purified by electroelution from agarose gels into Whatman 3 MM paper strips backed by dialysis tubing. The fragments were recovered from the paper and tubing by 3-4 washings with 0.1-0.2 mL volumes of a solution which contained 0.1M NaCl, 50 mM Tris-HCl (pH 8.0) and 1 mM EDTA. Finally, the fragments were extracted with phenol/chloroform/isoamyl alcohol, precipitated with ethanol and redissolved in a small volume of TE buffer.

F. Construction of *Pichia pastoris* Library in *E. coli*

For the *Pichia pastoris* DNA-YEp13 library construction, 100 µg of YEp13 was digested to completion with BamHI and treated with calf intestinal alkaline phosphatase to remove the terminal 5' phosphate from the DNA. A 100 µg aliquot of wild type *Pichia pastoris* DNA from *Pichia pastoris* NRRL Y-11430) was partially digested with 10 units of Sau3A I by incubation for 5 minutes at 37° C. in a total volume of 1 mL. Fragments of 5 to 20 kbp were size selected by centrifugation through 5-20% sucrose gradients. One µg of the vector and 2 µg of the Pichia Sau3AI fragments were mixed with 20 units of T4 DNA ligase (Bethesda Research Laboratories) in a total volume of 200 µL and incubated overnight at 4° C. The ligated DNAs were transformed into *E. coli* by adding the entire ligation reaction mix to 2 mL of competent *E. coli* 848 cells and incubating for 15 minutes at 0° C. The mixture was warmed to 37° C. for 5 minutes after which time 40 mL of LB medium was added and the 37° C. incubation continued for an additional 1 hour. Ampicillin was then added to give a total concentration of 100 µg/mL and the incubation continued for a second hour. Finally, the cells were centrifuged for 10 minutes at 3,000 g, resuspended in 1 mL of fresh LB medium and spread in equal aliquots on 10 LB agar plates containing 100 µg/mL of ampicillin. The approximately 50,000 colonies which resulted were scraped from the plates and a portion of the cells was inoculated into 500 mL of the supplemented 2B medium at a starting $A_{550}$ of about 0.1. The culture was grown and plasmid was extracted as described above. Of the colonies which were pooled for the library, 96 out of 100 tested were tetracycline sensitive and 7 out of 10 examined contained plasmids with insert DNA.

G. Southern Hybridizations

Hybridizations were carried out by the method of Southern (1975). For transfer of large or supercoiled DNA molecules to nitrocellulose, DNA was first partially hydrolyzed by soaking agarose gels in 0.25M HCl for 10 minutes prior to alkali denaturation. All hybridizations of labelled fragments were performed in the presence of 50% formamide, 6× SSC, 5× Denhardt's, 0.1% SDS, 1 mM EDTA, and 100 µg/mL denatured herring sperm DNA at 42° C. Post-hybridization washes for hybridization of labelled fragments from the *S. cerevisiae* HIS4 gene to *Pichia pastoris* DNA were carried out under the low stringency conditions of 2× SSC, 1 mM EDTA, 0.1% SDS and 1.0% sodium pyrophosphate at 55° C.

H. $^{32}$P-Labelling

Nick translations were carried out according to the procedure of Rigby et al (1977).

I. Yeast Transformations

*S. cerevisiae* transformations were carried out by the spheroplast generation method of Hinnen et al (1978).

*Pichia pastoris* transformations were performed following the procedure described above.

J. Isolation of Pichia HIS4 Gene

DNA fragments which contained the Pichia HIS4 gene were isolated from a Pichia DNA library by their ability to complement *S. cerevisiae* his4 strains. The library was composed of 5-20 kb Sau3AI partial digestion fragments of wild type Pichia DNA inserted into the BamHI site of the *S. cerevisiae-E. coli* shuttle vector YEp13. Spheroplasts of *S. cerevisiae* NRRL Y-15859 (5799-4D; a his4ABC− strain) were generated by the technique of Hinnen et al (1978), mixed with the Pichia DNA library and allowed to regenerate in a medium deficient in histidine. The transformation resulted in about $1 \times 10^3$ prototrophic yeast colonies from a population of $5 \times 10^7$ total regeneratable spheroplasts. Total yeast DNA was extracted from 20 of the His+ colonies and transformed into *E. coli*. Seventeen of the yeast DNA preparations produced ampicillin resistant colonies and each contained plasmid comprised of YEp13 plus insert DNA. To confirm that the His+ transforming plasmids contained the Pichia HIS4 gene and not a DNA fragment with suppressor activity, restriction digests of the plasmids were hybridized to a labelled DNA fragment containing a large portion of the *S. cerevisiae* HIS4 gene and washed at low stringency. Each of the plasmids which complemented the his4 *S. cerevisiae* strains contained sequences which hybridized to the *S. cerevisiae* HIS4 gene.

One of the His+ transforming plasmids was selected for further characterization. A detailed restriction map of the 6.0 kbp fragment is presented in FIG. 3. The smallest subfragment capable of transforming the his4 mutant NRRL Y-15851 (GS115) at high frequency was determined to be 2.7 kbp BglII fragment (see FIG. 3) by transforming GS115 with portions of the 6.0 kbp fragment. This BglII fragment was also capable of transforming the *S. cerevisiae* his4 mutant NRRL Y-15859 at high frequency. Thus the HIS4 gene isolated and characterized in accordance with the invention is believed to contain the HIS4A, HIS4B and HIS4C gene functions which have been identified in *S. cerevisiae*, i.e., phosphoribosyl-ATP-cyclohydrase, phosphoribosyl-ATP-pyrophosphohydratase and histidinol dehydrogenase, respectively.

EXAMPLE III

Construction Of Regulatory Region-LacZ Gene Fusions

In order to identify a DNA fragment which contains the Pichia HIS4 promoter and regulatory sequences, plasmid pYJ8 and restricted with EcoRI and PvuII and electroeluted. A 600 bp fragment of Pichia DNA was collected and ligated into plasmid pBPf1 which had been cleaved at the polylinker site with EcoRI and SmaI. The resulting plasmid, pBPf3, was used to transform *Pichia pastoris* NRRL Y-15851, which was then used in further studies directed to the production of β-galactosidase under the control of the Pichia HIS4 regulatory region.

EXAMPLE IV

Expression of β-Galactosidase Under Amino Acid Control

A. Plate Culture Assays

P. pastoris NRRL-Y-15851 transformed with pBPf3 was streaked onto YPD and SD medium 2% agar plates supplemented with 0.4 µg/mL of biotin and 40 µg/mL of Xgal (5-bromo-4-chloro-3-indolyl-β-D-galactoside). The SD-containing plates were adjusted to a pH of 7 by addition of monobasic potassium phosphate. The principle of the Xgal assay is that β-galactosidase, if present in the cells, will react with Xgal to produce a compound with a blue color. The resulting blue color can be visually detected. Blue color developed in the pBPf3 transformed P. pastoris cells within about 4–5 hours on the minimal (SD medium) plate, while about 1 week incubation was required for blue color development to occur on plates containing the rich (YPD) medium. As controls, neither untransformed P. pastoris cells, nor pBPf1 transformed P. pastoris cells nor pBPf2 (a derivative of pBPf1 with a 400 bp $R_1$–$B_2$ fragment from the 5' terminus of the Pichia HIS4 gene) transformed P. pastoris cells turned blue under any conditions tested. These observations suggest that the 600 bp $R_1$–$R_2$ Pichia HIS4 fragment-LacZ gene fusion is expressed and is regulated under an amino acid control system.

B. Liquid Culture Assays

P. pastoris NRRL Y-15851 was transformed with plasmid pBPf3. Transformed cells were inoculated into SD medium supplemented with 0.4 µg/mL of biotin and grown at 30° C. with shaking until the $A_{600}$ per mL of solution was about 0.7. Then 3.5 mL aliquots of culture were added to each of 2 flasks containing 96.5 mL of one of the following media:

I. SD medium plus 0.4 µg/mL biotin; and
II. HAM.

These 2 cultures were grown logarithmically at 30° C. with shaking for 80 hours. Samples were removed after specific time periods and assayed for β-galactosidase.

| z-buffer | | Final concentration |
|---|---|---|
| $Na_2HPO_4 . 7H_2O$ | 16.1 g | 0.06 M |
| $NaH_2PO_4$ | 5.5 g | 0.04 M |
| KCl | 0.75 g | 0.01 M |
| $MgSO_4 . 7H_2O$ | 0.246 g | 0.001 M |
| 2-mercaptoethanol | 2.7 mL | 0.05 M |
| fill up to 1L; | | |
| pH should be 7 | | |

O-Nitrophenyl-β-D-galactoside (ONPG):
Dissolve 400 mg ONPG (Sigma N-1127) in 100 mL of distilled water to make a 4 mg/mL ONPG solution.

2. Assay Procedure:
   i. Withdraw an aliquot from the culture medium (0.1–0.5 $OD_{600}$ of yeast cells), centrifuge and wash cell pellet with water.
   ii. Add 1 mL of Z buffer to the cell pellet, 30 µL of $CHCl_3$ and 30 µL of 0.1% SDS, vortex, incubate 5 minutes at 30° C.
   iii. Start reaction by adding 0.2 mL of ONPG (4 mg/mL), vortex.
   iv. Stop reaction by adding 0.5 mL of a 1M $Na_2CO_3$ solution at appropriate time points $A_{420}<1$).
   v. Read absorbance of supernatant at 420 nm.
3. Calculation of β-galactosidase Units:

1 U = 1 nmole of orthonitrophenol (ONP) formed per minute at 30° C. and a pH 7. 1 nmole of ONP has an absorbance at 420 nm ($A_{420}$) of 0.0045 with a 1 cm pathlength; thus, an absorbance of 1 at 420 nm represents 222 nmole ONP/mL, or 378 nmole/1.7 mL since the total volume of supernatant being analyzed is 1.7 mL. Hence, Units expressed in the Tables are calculated:

$$U = \frac{A_{420}}{t(\text{min})} \times 378$$

Results of these experiments are summarized in the Table.

TABLE

| Medium | β-galactosidase activity (u/$A_{600}$), hrs. | | |
|---|---|---|---|
| | 24 | 45 | 72 |
| SD | .63 | 113 | 173 |
| HAM | 97 | 280 | 225 |

The results presented in the Table indicate that β-galactosidase is expressed under control of the Pichia HIS4 promoter region.

EXAMPLE V

Integrative Transformation of Pichia

To demonstrate integrative recombination of a vector into the genome of P. pastoris, P. pastoris NRRL Y-15851 was transformed with plasmid pYJ8 (see FIG. 4), a vector which can be selected in his4 Pichia hosts such as NRRL Y-15851. Plasmid pYJ8 has approximately 6.0 kbp of DNA sequences which are homologous to the Pichia genome. Further, plasmid pYJ8 has no detectable autonomous replication sequence activity in Pichia hosts. The transformation of NRRL Y-15851 with pYJ8 resulted in the formation of about 50 His+ colonies per µg of pYJ8. The presence of pYJ8 sequences in the P. pastoris genome was demonstrated as follows: Transformant colonies were picked from the regeneration agar plate and streaked onto an SD medium agar plate. The SD plate was incubated at 30° C. for 3 days after which time a single colony of each transformant was inoculated into a flask of IMG medium. The IMG cultures were grown at 30° C. with shaking to an $A_{600}$ of about 1–2 and then harvested by centrifugation. DNA from the yeast cultures was extracted as described above, and 1–2 µg of each DNA (unrestricted) was electrophoresed at 30 Volts and 30 mAmps for 10–15 hours into 0.8% agarose gels, transferred to nitrocellulose and hybridized to $^{32}$P-labelled pBR322 as described above. As controls, a sample containing 10 ng of plasmid pYJ8 isolated from E. coli and a sample containing 1–2 µg of untransformed Pichia pastoris GS115 DNA were electrophoresed in parallel with the experimental samples. In each of the pYJ8-Pichia transformants examined, the labelled pBR322 probe hybridized to the high molecular weight Pichia chromosomal DNA. In the control, no labelled probe hybridized to the untransformed Pichia DNA.

The examples have been provided merely to illustrate the practice of my invention and should not be read so as to limit the scope of my invention or the appended claims in any way. Reasonable variation and modification, not departing from the essence and spirit of my invention, are contemplated to be within the scope of the patent protection desired and sought.

BIBLIOGRAPHY

Birnboim and Doly (1979) Nucl. Acids Res. 7, 1513-1523.
Hinnen et al (1978) Proc. Nat. Acad. Sci., USA 75, 1929-1933.
Rigby et al (1977) J. Mol. Biol. 113, 237.
Southern (1975) J. Mol. Biol. 98 503-517.

I claim:

1. A method for the isolation of functional genes from yeast strains of the genus Pichia by complementation comprising:
   (a) preparing a library by treating Pichia total DNA with an appropriate restriction enzyme to give Pichia DNA fragments and cloning said DNA fragments into a Saccharomyces cerevisiae—Escherichia coli shuttle vector;
   (b) transforming with said library a mutant Saccharomyces cerevisiae host strain which has a selectable phenotype as a result of a defect in at least one gene product;
   (c) growing the transformed strains under selective growth conditions; wherein said selective growth conditions do not provide the conditions required by the defective host strain for growth and wherein the transformant selected for comprises a plasmid which contains a Pichia gene which complements the Saccharomyces cerevisiae gene defect;
   (d) isolating plasmid DNA from said selected transformed strains; and
   (e) recovering Pichia functional gene DNA inserts from said plasmid DNA.

2. A method in accordance with claim 1 wherein said Saccharomyces cerevisiae—Escherichia coli shuttle vector is YEp13 (ATCC37115).

3. A method in accordance with claim 1 wherein said host Saccharomyces cerevisiae strain is defective in an amino acid biosynthetic pathway.

4. A method in accordance with claim 3 wherein said host Saccharomyces cerevisiae strain is defective in the HIS4 gene.

5. A method in accordance with claim 4 wherein said host strain is Saccharomyces cerevisiae NRRL Y-1589.

6. A method in accordance with claim 4 wherein said selective growth conditions comprise yeast minimal media absent histidine.

7. An isolated DNA fragment obtained from Pichia pastoris which comprises the gene encoding histidinol dehydrogenase.

8. An isolated DNA fragment in accordance with claim 7 further coding for the production of phosphoribosyl-ATP-cyclohydrase and phosphoribosyl-ATP-pyrophosphohydratase.

9. An isolated DNA fragment in accordance with claim 7 further comprising a DNA fragment wherein said gene is characterized by the restriction map in FIG. 3b of the drawings.

10. An isolated DNA fragment in accordance with claim 7 further comprising flanking regions of chromosomal DNA as characterized by the restriction map in FIG. 3a of the drawings.

11. An isolated DNA fragment comprising a regulatory region derived from the HIS4 gene locus of Pichia pastoris wherein said regulatory region is responsive to the concentration of histidine in the culture medium with which a host organism for said DNA fragment is in contact and wherein said regulatory region is capable of controlling the production of polypeptides when positioned at the 5' end of the DNA which codes for the production of said polypeptides.

12. An isolated DNA fragment in accordance with claim 11 wherein said fragment is characterized by the restriction map in FIG. 3c of the drawings.

13. An isolated DNA fragment in accordance with claim 11 comprising the LacZ gene positioned at the 3' end of said regulatory region.

14. An isolated DNA fragment in accordance with claim 13 wherein said fragment is characterized by the 4.2 kbp EcoRI-NruI fragment of the restriction map in FIG. 6 of the drawings.

15. Hybrid plasmid pYJ8 having the restriction map shown in FIG. 4 of the drawings.

16. Hybrid plasmid pBPf3 having the restriction map shown in FIG. 6 of the drawings.

17. Escherichia coli NRRL B-15889 (LE392-pYJ8).

18. Escherichia coli NRRL B-15892 (LE392-pBPf1).

19. A process for isolating a plasmid pYJ8 containing the Pichia pastoris HIS4 gene comprising:
   (a) culturing Escherichia coli NRRL B-15889 (LE392-pYJ8) in a nutrient medium;
   (b) disrupting the cultured cells; and
   (c) recovering plasmid pYJ8 from the disrupted cells.

20. A process in accordance with claim 19 further comprising:
   (d) digesting plasmid pYJ8 with one of the restriction enzyme combinations selected from the group consisting of;
   NruI,
   EcoRV and SphI, and
   NruI and SphI; and
   (e) recovering a DNA fragment of about 6.0 kbp.

21. A process in accordance with claim 19 further comprising:
   (d) digesting plasmid pYJ8 with the restriction enzyme BglII; and
   (e) recovering a DNA fragment of about 2.7 kbp.

22. A process in accordance with claim 19 further comprising:
   (d) digesting plasmid pYJ8 with the restriction enzymes EcoRI and PvuII; and
   (e) recovering a DNA fragment of about 600 base pairs.

23. A process for controlling the expression of heterologous polypeptide in a transformed Pichia pastoris strain comprising culturing said transformed Pichia pastoris strain in the presence or absence of histidine, wherein said transformed Pichia pastoris has been transformed with a hybrid plasmid; wherein said hybrid plasmid comprises a regulatory region derived from the HIS4 gene locus of Pichia pastoris and a heterologous polypeptide coding region; wherein said regulatory region is capable of controlling the production of said heterologous polypeptide when positioned at the 5' end of said heterologous polypeptide DNA coding region; wherein said polypeptide DNA coding region is expressed in the absence of histidine and not expressed in the presence of histidine.

24. A process according to claim 23 wherein said plasmid is plasmid pBPf3.

* * * * *